US012672645B2

(12) United States Patent　　　　(10) Patent No.:　US 12,672,645 B2
Bolard et al.　　　　　　　　　　　(45) Date of Patent:　　Jul. 7, 2026

(54) AUTOMATED INSECT FARMING INSTALLATION

(71) Applicant: NASEKOMO B.V., Amsterdam (NL)

(72) Inventors: Marc Louis Raymond Bolard, Sofia (BG); Kamen Nikolaev Vasilev, Sofia (BG)

(73) Assignee: NASEKOMO B.V., Amsterdam (NL)

( * ) Notice: Subject to any disclaimer, the term of this patent is extended or adjusted under 35 U.S.C. 154(b) by 0 days.

(21) Appl. No.: 18/811,458

(22) Filed: Aug. 21, 2024

(65) Prior Publication Data

US 2025/0064035 A1　Feb. 27, 2025

(30) Foreign Application Priority Data

Aug. 22, 2023　(EP) .................................... 23192781

(51) Int. Cl.
　　*A01K 67/30*　　　(2025.01)
　　*A01K 67/36*　　　(2025.01)
(52) U.S. Cl.
　　CPC .............. *A01K 67/30* (2025.01); *A01K 67/36* (2025.01)
(58) Field of Classification Search
　　CPC ................................. A01K 67/30; A01K 67/36
　　See application file for complete search history.

(56)　　　　　References Cited

U.S. PATENT DOCUMENTS

| | | | | | |
|---|---|---|---|---|---|
| 2020/0205369 A1 * | 7/2020 | Calis | .................... | A01K 1/0047 |
| 2020/0323173 A1 * | 10/2020 | Sabeg | .................. | A01K 67/368 |
| 2021/0368754 A1 * | 12/2021 | Yeh | ........................ | A01M 1/106 |
| 2022/0061232 A1 * | 3/2022 | Whelan | ................... | A01K 67/30 |
| 2024/0260554 A1 * | 8/2024 | Duan | ..................... | A01K 67/30 |

FOREIGN PATENT DOCUMENTS

| | | | | |
|---|---|---|---|---|
| CN | 108029641 A | 5/2018 | | |
| CN | 110074066 A | 8/2019 | | |
| CN | 110612944 A | 12/2019 | | |
| CN | 111713459 A | 9/2020 | | |
| CN | 113057145 A | 7/2021 | | |
| CN | 113728976 A | 12/2021 | | |
| EP | 3747264 A1 | 12/2020 | | |
| EP | 3 968 476 A1 | 3/2022 | | |
| EP | 4098114 A1 | 12/2022 | | |
| KR | 20180047041 A | * 5/2018 | .......... | A01K 67/033 |
| WO | WO2014171829 A1 | 10/2014 | | |
| WO | WO2019022596 A1 | 1/2019 | | |
| WO | WO2020246878 A1 | 12/2020 | | |
| WO | WO2020256541 A1 | 12/2020 | | |

OTHER PUBLICATIONS

Extended European Search Report dated Jan. 19, 2024 for European Application No. 23192781.5.
The Extended European Search Report for European Patent Application No. 23 192 781.5, dated Aug. 13, 2025.

* cited by examiner

*Primary Examiner* — Monica L Perry
*Assistant Examiner* — Aaron M Rodziwicz

(57)　　　　　ABSTRACT

An insect farming installation comprises: a module comprising continuous profiled containers, each continuous profiled containers being configured to be filled with substrate containing larvae, wherein the continuous profiled containers are vertically superimposed to one another, and wherein at least some of the containers are configured to be filled with substrate in a way adapted to maximize an age difference of the larvae contained in the substrates respectively filling two consecutive containers, and wherein the containers are at least partially made with a thermally conductive material.

14 Claims, 3 Drawing Sheets

AUTOMATED INSECT FARMING INSTALLATION

FIELD OF THE INVENTION

The present invention relates to an automated insect farming installation, and particularly to an automated insect farming installation for the bioconversion of organic matter.

CROSS-REFERENCE TO RELATED APPLICATION

This application claims the priority to European application No. EP23192781.5 filed on Aug. 22, 2023, the contents of which are incorporated by reference.

BACKGROUND OF THE INVENTION

Some insects efficiently convert organic secondary streams into protein, which can be used for animal feeding. One solution to recycle these secondary biomasses is to set up a biological treatment by replicating at a large scale the natural process of organic biomass cycle. Such process is called bioconversion.

A whole farming cycle is made of 4 steps:

Step 1: Organic waste is collected from agricultural co-products for example, like breweries or ethanol plants.

Step 2: Insects are reared in a highly bio-secure environment and fed with the organic waste.

Step 3: Insects are collected from the remaining frass.

Step 4: In a dry rendering process, insects are dried, and a protein meal and a fatty fraction are separated and further processed into animal feed ingredients. In a wet rendering process, the insects may first be cooked and grinded and then a separation of the solids, oils and water is performed to finally dry the solid fraction.

Step 5: On the other hand, the insect frass is extracted to be used as organic fertilizer for agricultural plantation.

Thus, the organic fertilizer is useful for vegetable farming, and the protein-rich meal and the insect oil are produced to feed animals.

Such process makes it possible to artificially reproduce the complete natural cycle of organic matter. Some pollution and waste of resources may then be avoided by replicating the whole natural cycle.

Among the advantages of such process, the environmental impact is highly reduced, in terms of water consumption, agricultural land usage, feed consumption.

The above step 2 can be divided into two phases: A first phase comprises a maturation of insect eggs until the larvae hatch and grow for a few days, for example five days. A second aging phase in a substrate lasts for 4 to 15 days, for example 7 to 8 days, and results in mature larvae and frass. The present invention especially concerns the second aging phase.

Nowadays, some insect farming installations 1 are developed to answer to the problematics of providing an environment promoting the bioconversion process of the larvae while improving the overall efficiency of the installation in terms of cost, energy consumption and harvested larvae.

For example, document WO 2019/022596 describes an example of an insect farming installation in which are provided clusters of one or more stacks of crates with immature phases of insects. The installation comprises a climate control system which comprises two ventilation openings per crates, and an aeration system adapted to deliver conditioned air according to properties in relation to one or more parameters of the stacks.

However, this document does not allow to answer to the problematics of improving the overall efficiency of the installation. There is then a need to provide a farming installation that would promote the bioconversion process of the larvae during the second aging phase and that would improve the overall efficiency of said installation.

BRIEF SUMMARY OF THE INVENTION

To this aim, the invention relates to an insect farming installation comprising: a module comprising continuous profiled containers, each continuous profiled containers being configured to be filled with substrate containing larvae, wherein the continuous profiled containers are vertically superimposed to one another, and wherein at least some of the containers are configured to be filled with substrate in a way adapted to maximize an age difference of the larvae contained in the substrates respectively filling two consecutive containers, and wherein the containers are at least partially made with a thermally conductive material.

According to different aspects, it is possible to provide the one and/or the other of the characteristics below taken alone or in combination.

In an embodiment, all the containers are configured to be filled with substrate in a way adapted to maximize an age difference of the larvae/insect contained in the substrate filling two consecutive containers.

In an embodiment, the containers are configured to be filled such that a container filled with substrate containing younger larvae is located directly above a container filled with substrate containing older larvae.

In an embodiment, the filling of two consecutive containers is configured to be performed by:

filling a first container with substrate containing seeded larvae, leaving a second container empty, said second container being located above the and being consecutive to said first container, after a chosen time, filing said second container with substrate containing seeded larvae, said chosen time corresponding to a time needed by the larvae to become mature larvae.

In an embodiment, the installation comprises a climate control system comprising an air injection subsystem, said air injection subsystem comprising a pair of incoming air outputs configured to inject air towards the containers, each incoming air outputs of said pair of incoming air outputs facing each other such that the injection subsystem is configured to inject air according to a turbulent flow.

In an embodiment, the air injection subsystem comprises one pair of incoming air outputs per containers, each pair of incoming air outputs being configured to inject air on the substrate contained in the corresponding container according to the turbulent flow.

In an embodiment, the air injection subsystem comprises a plurality of pairs of incoming air outputs per containers, each pair being disposed equidistantly from one another according to a longitudinal direction of said container.

In an embodiment, the climate control system further comprises an air extraction subsystem comprising at least one air extraction entry adapted to extract the air injected by the air injection subsystem from the farming installation.

In an embodiment, the air extraction subsystem comprises a plurality of air extraction entries per containers, said air extraction entries being adapted to extract the air injected by the air injection subsystem, an air extraction entry being placed between each pair of incoming air outputs per container.

In an embodiment, the air injection subsystem is configured to inject air pumped from outside the farming installation, wherein the extracted air is warmer than the injected air and wherein the air extraction subsystem is configured to heat the air pumped by the air injection subsystem with the extracted air before its injection in the farming installation.

In an embodiment, at least a portion of the extracted air is configured to be recycled and injected in the air injection subsystem.

In an embodiment, the installation comprises a mobile workstation,

Said mobile workstation comprising a displacement system, said mobile workstation being configured to move above the containers by mechanical cooperation with a guiding system of said automated insect farming installation, and Said mobile workstation comprising an active system configured to perform an action on the substrate, said action favouriting a growth of the larvae contained in the substrate.

In an embodiment, the active system comprises at least one plough configured to plough the substrate.

In an embodiment, the ploughing is configured to be made according to a static schedule and/or according to a dynamic schedule, said dynamic schedule being dynamically adjusted according to a data-driven system.

In an embodiment, a length of each container is equal or above 10 meters.

BRIEF DESCRIPTION OF THE DRAWINGS

Embodiments of the invention will be described below with reference to the drawings, described briefly below.

Figure 1:
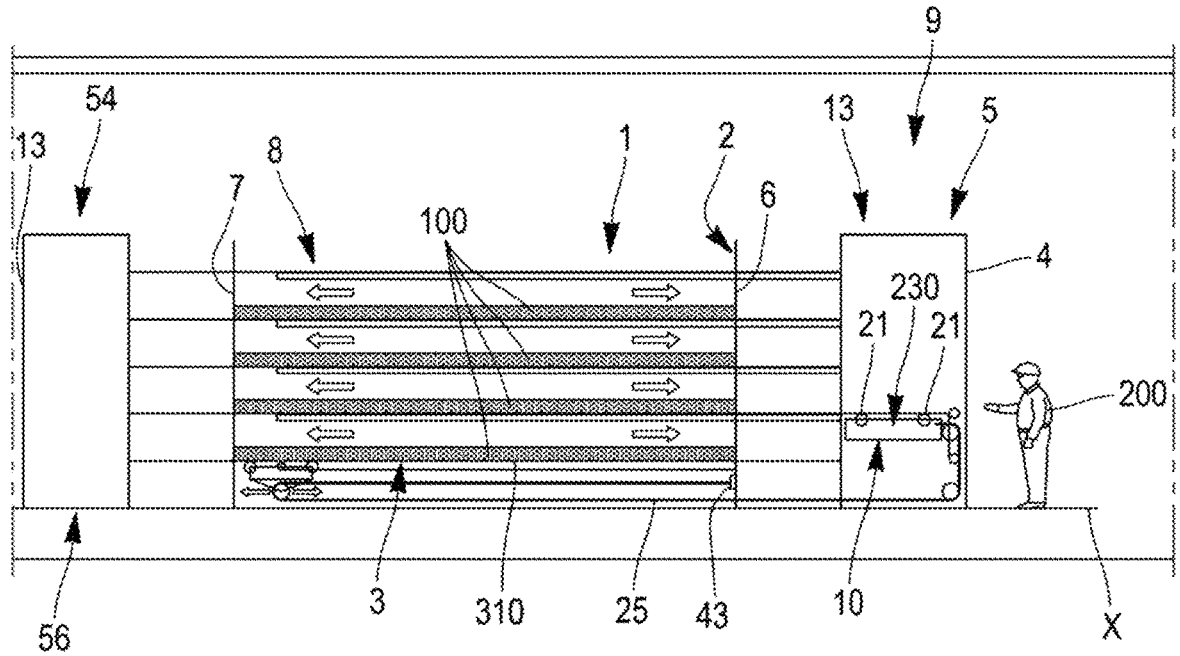
FIG. 1 represents an overall view of a farming installation according to a non-limitative embodiment.
Figure 2:
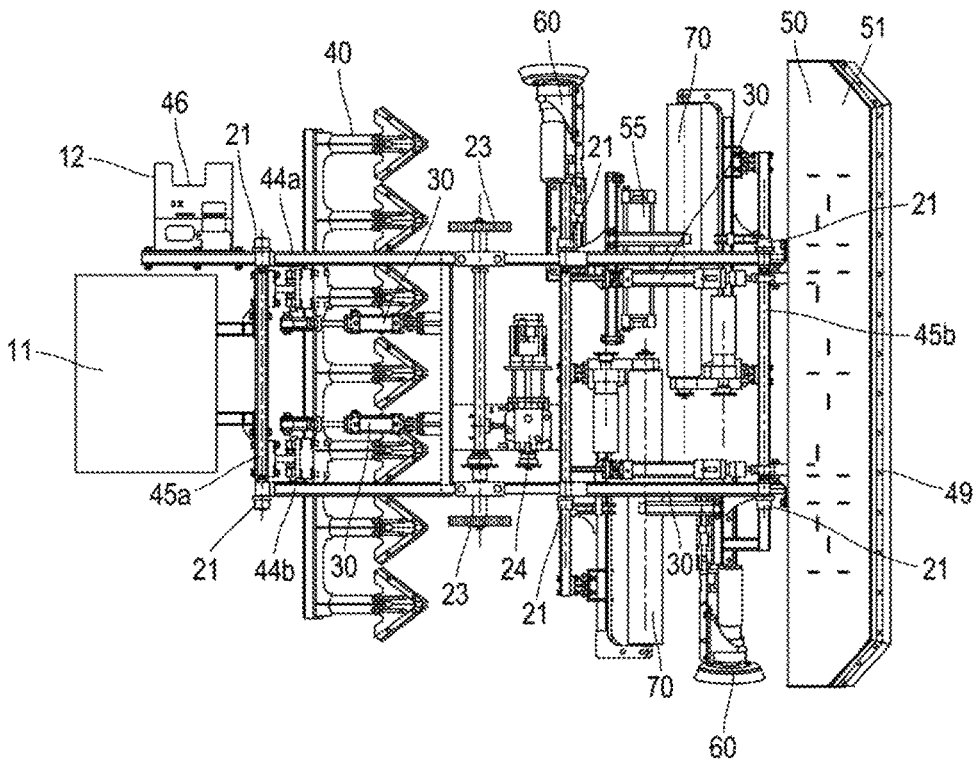
FIG. 2 represents a top view of a mobile workstation according to an embodiment.

In the drawings, identical references designate identical or similar objects.

DETAILED DESCRIPTION OF THE INVENTION

FIG. 1 schematically illustrates a farming installation 11 dedicated to the culture of insects.

The farming installation 1 comprises a breeding module 8, an entry module 9, an output module 54, an entrance and an opposed output end 13. The breeding module 8 comprises a structure 2, the structure 2 comprising two lateral vertical frames. Between the two lateral vertical frames, a plurality of horizontal containers 310 are fixed one above the other. Furthermore, according to a configuration, several containers 310 may be aligned with each other according to the longitudinal direction, between the two vertical frames. In another configuration, one single container 310 extends from one end to the other end of the farming installation 1 along the longitudinal direction.

The containers 310 extend along a longitudinal direction and are profiled along the longitudinal direction. For example, the containers 310 have a U-shaped cross-section transverse to the longitudinal direction. The containers 310 are destined to be filled with a substrate that will be described in more details below.

The farming installation 1 further comprises a pair of rails fixed above each container, the pair of rails extending between the two lateral vertical frames. Each rail 22 for example comprises a toothed rack extending longitudinally along the rail.

The farming installation 1 further comprises a mobile workstation 10. The mobile workstation 10 is able to move along the rails, above the containers 310. The mobile workstation 10 may be used to treat the containers 310 or the substrate contained therein, which are later called a "work area 3". A source of energy 43, such as for example electrical energy and/or pneumatic energy, is also provided. The mobile workstation 10 is supplied by the source(s) of energy through suitable cables.

Among many functionalities that the mobile workstation 10 may perform, said mobile workstation 10 may be able to fill the containers 310 with substrate brought into the farming installation 1 toward the entrance and to empty the containers 310 by removing the substrate through the opposed output end 13. The substrate may be supplied by a substrate supply system (not shown).

In one embodiment, to position the mobile workstation 10 at the entrance of each work area 3, as shown on FIG. 1, the farming installation 1 further comprises a lift system. The lift system is provided at a first longitudinal end of the farming installation 1. In one example, the lift system is part of the entry module 9 of the farming installation 1, and facing the entrance end of the breeding module 8. In this embodiment, the lift system may be used to bring the substrate into the containers 310.

The lift system comprises a static structure 32 and a vertically movable part 230 adapted to move vertically with respect to the static structure 32, for example by means of an engine (not shown).

When the mobile workstation reaches a level associated to an intended work, the mobile workstation 10 is moved with respect to the static structure. The mobile workstation 10 is moved down until it is facing the guide rail 22.

The mobile workstation 10 can thus be controlled to be moved along the rails 22, whereby it is disassembled from the vertically movable part 230.

When the mobile workstation 10 finishes working at this work area 3, it is assembled to the lift system according to a reverse order of the above-described steps.

The mobile workstation 10 is able to move horizontally over the flat surface of the containers 310 of the farming installation 1 and also vertically thanks to the lift system 5. The motion of the mobile workstation 10 is defined as "forward" when the mobile workstation 10 moves in the direction from the lift system toward the output module 54, and as "backward" when the mobile workstation 10 moves in the direction from the output module 54 toward the lift system.

Figure 3:
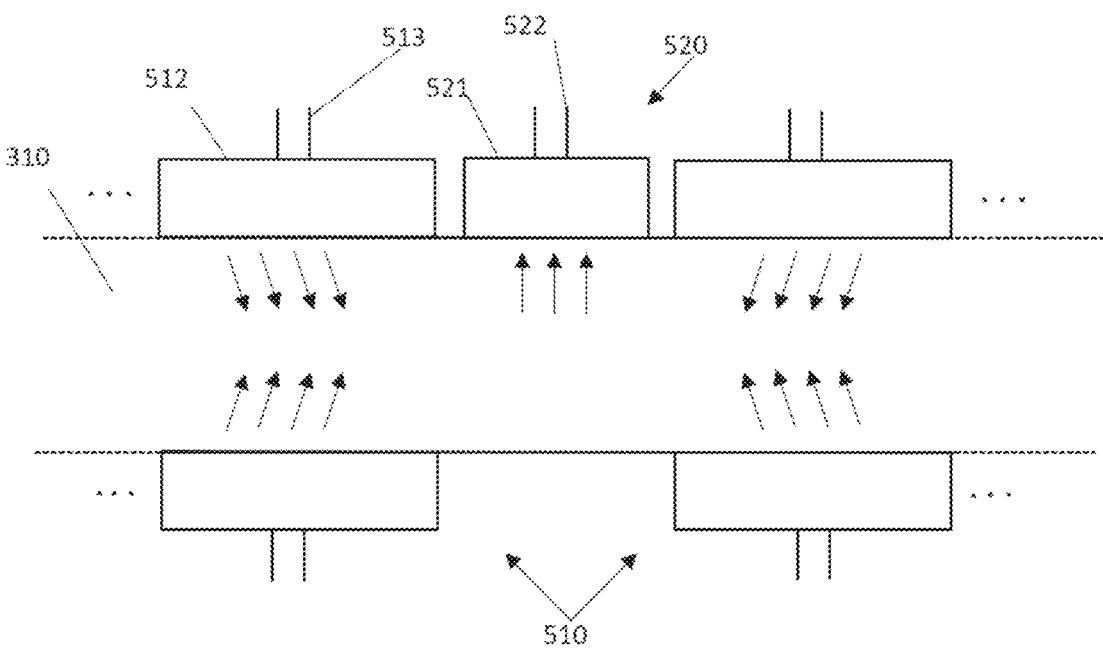
FIG. 3 represents a top view of a farming installation with a climate control system according to an embodiment.

As shown on FIG. 3, the mobile workstation 10 comprises a structure carrying the various other functional components of the mobile workstation 10. The structure for example comprises a rigid frame or may alternatively comprise other mechanical structural elements such as plates. The frame for example comprises two side longitudinal parallel beams 44a, 44b assembled to one another through cross-beams 45a, 45b. There might be more than two cross beams. The frame carries a connection system 12 adapted to connect the workstation to one or more cables. For example, the frame carries an electronic connection device 46 comprising the connection system 12. The cables comprise an electrical cable with power, signal lines such as electrical or optical signal lines, and/or a comprised air lines, one or more liquid lines, etc. The connection system 12 is provided at the rear of the frame, and the cables extend backward from the mobile workstation 10.

The frame carries the control system of the mobile workstation 10. The control system comprises a controller 11, for example a computer able to deliver control signals to other components of the mobile workstation 10. The control system is provided close to the connection system, for example at the rear of the mobile workstation 10.

The frame carries at least three suspension wheels 21 unaligned and defining one horizontal moving place. The frame further carries at least one driving wheel 23.

The suspension wheels 21 are able to be placed and to run on the rails. In one embodiment, six suspension wheels 21 are separated into two groups of three aligned wheels. The size and lateral spacing of the wheels are adapted to the two rails. The at least one driving wheel 23 is connected to an engine to rotate the driving wheel in both rotating directions. The driving wheel has a toothed surface able to interact with the fixed linear toothed rack running longitudinally. The interaction between the rack and the toothed surface of the wheel allows a precise positioning of the mobile workstation 10.

In an embodiment, two driving wheels 23 are positioned on the lateral sides of the mobile workstation 10, along a horizontal line perpendicular to the movement direction and crossing the centre of gravity of the mobile workstation 10. Thus, the stresses related to the motion of the mobile workstation 10 at the level of the suspension wheels are minimized.

The driving wheel can move the mobile workstation 10 in the forward and backward directions. The controller is able to receive a movement command from the central control and to deliver signals to activate the supply of energy to the engine, hence causing rotation of the driving wheel in either rotation direction.

The alimentation source of the engine 24 alimenting the driving wheel 23 is for example electricity provided through the cable, from the source 43 of electricity of the mobile workstation 10.

The engine 24 and driving wheels 23, as well as the transmission of movement from the engine to the driving wheels, form an example of a displacement system to move the mobile workstation 10.

The mobile workstation 10 comprises tools able to perform one action onto the substrate. The mobile workstation 10 further comprises actuators arranged to move respective tools from an upper stand-by position to a lower active position.

Actuators can be cylinders 30 activated by different means such as compressed air, electricity, hydraulic power, etc.

In this non-limiting embodiment, the cylinders 30 are powered by compressed air. The compressed air is provided through the compressed air pipe, from the source of compressed air to the mobile workstation 10. The mobile workstation 10 may bear a compressed air reserve stock 55. The air reserve stock is designed to provide compressed air at a higher pressure than can be provided from the source. The air reserve stock 55 may be used to provided energy to the cylinders upon need and can be filled from the source when partially or totally depleted.

Some tools of the mobile workstation 10 are passive tools: being in the lower active position, combined with the movement of the mobile workstation 10 in its longitudinal direction, action of the tool is applied on the substrate.

Some tools are active tools: in addition to a passive tool action mode, the active tools can be moved in action mode by an engine to give them, for example, a rotation movement. Thus, the efficiency of the tool is increased.

For example, the tools comprise ploughs 40, a pusher 50 and brushes 60, 70.

In an embodiment, four brushes 60, 70 may be used, for example two lateral brushes 60, 70 and two bottom brushes 60, 70. The lateral brushes 60, 70 are designed to brush the lateral wings of the container 310 and the bottom brushes 60, 70 are designed to brush the bottom of the container 310. Each brush can be moved by a dedicated electric engine. Brushes 60, 70 can rotate alternatively in the two opposite rotation directions for a better brushing efficiency.

To cover the width of the container, at least one plough 40, and preferably several ploughs 40, f, are mounted on a movable stem. The ploughs 40 can be moved vertically from an upper standby position to their lower active position by compressed air cylinders 30.

The ploughs 40 can be oriented either in the forward direction, or the backward direction, or in both directions. Ideally, in both directions, the ploughs 40 of the backward direction are not aligned with the ploughs 40 of the forward direction. Thus, the substrate is ploughed along different lines, enhancing the ploughing effect.

Ploughing prevents crusting on the surface of the substrate and enhances gas exchange with the outside, thereby promoting the bioconversion process of the larvae, as it will be explained in more details below.

The pusher 50 is at the front of the mobile workstation 10. The pusher 50 comprises a sensibly flat plate. The size of the pusher 50 is adapted to match the container's: The length and height of the pusher 50 are adapted to cover the transversal section of the container 310 up to the level of the substrate. The pusher 50 is able to be oriented with respect to a horizontal axis perpendicular to direction of movement of the mobile workstation 10. The orientation of the pusher 50 with respect to this axis may be modified by actuators.

The pusher 50 can be positioned in an upper position, wherein the pusher 50 is above the surface of the substrate, or in a lower position wherein the bottom of the pusher 50 can touch the internal surface of the bottom of the container.

The front edge of the pusher 50 has a sharp shape in order to shear the substrate when moving from the upper position to the lower position. The front edge of the pusher 50 may comprise a metallic body covered with an elastomeric coating in order to seal the bottom of the pusher 50 to the bottom of the container 310 in the lower position. The actuators to move the pusher 50 between the upper and the lower positions are for example two compressed air cylinders 30. The power provided by the actuators has to be enough to enable the pusher 50 to cut through the substrate.

Thus, in the lower position, the pusher 50 can separate a portion of the substrate (to the right of the pusher 50) from the bulk of substrate (to the left of the pusher 50) and push it outside of the container 310. In fact, the container 310 can be long of several meters, for example between 10 meters and 50 meters, and contain substrate over a given thickness, 15 cm of substrate thickness for example. In that case, pushing in and out all the substrate of one container 310 requires such an energy that the structure of the mobile workstation 10 is not able to withstand the corresponding stresses. So, the substrate is installed in the container 310, and removed from the container 310, portion of substrate by portion of substrate. Each portion is about between 100 and 300 kg of substrate.

To push one portion of the substrate out of the container 310, the pusher 50 cuts through the substrate to its lower position, vertically oriented. The portion of substrate to be removed from the container 310 is in front of the pusher 50, and the mobile workstation 10 moves forward toward the output end 13.

To push one portion of the substrate into the container 310, the pusher 50 is in the lower position, vertically oriented, the portion of substrate to be positioned into the container 310 is in front of the pusher 50 at an entry position of the container, the mobile workstation 10 moves toward the position where the portion of substrate has to be placed.

Once the substrate is in place in a work area of a container 3, some steps of treating the substrate can be repeated as needed during the duration of the aging cycle. These actions are performed by activating different actuators of the mobile workstation 10. These actions may be launched based on a predetermined static schedule, or on a dynamic schedule, based on a data-driven system.

For example, one action is to plough the substrate. When a ploughing operation is decided, the ploughs 40 are moved to their lower active position. Forward movement of the mobile workstation 10 will then cause the ploughs 40 to shear through the substrate, promoting air exchanges and uncrusting the surface. After the ploughing operation is complete, the ploughs 40 are moved up to their upper passive position.

The possibility to plough the substrate allows for using a deeper substrate layer, for example up to 15 cm. In case no ploughing is applied, a substrate layer thickness could only reach 7-8 cm as beyond this depth the larvae cannot reach the bottom of the substrate, anaerobic fermentation processes start developing and the temperature of the substrate may quickly rise above 50 degrees centigrade. As a result, the nutrients in the bottom of the substrate are wasted and the larvae start escaping from the heat by climbing on the walls of the container 310 or they die because of the high temperature. Ploughing the thick layer of substrate allows the larvae to easily access the nutrients and convert them to body mass and facilitates the release of heat and metabolic gasses, such as carbon dioxide, ammonia, nitrite dioxide. The evacuation of metabolic gasses is advantageous since their presence in the substrate could inhibit the bioconversion. Indeed, the presence of metabolic gases in the substrate may imply too rare presence of oxygen in the substrate for the larvae/insects to grow. Also, the metabolic gases can be picked up by a climate control system 500 described in more detail below. The ploughing also enables to bring fresh air in the substrate, such as oxygen. Such bringing may limit the anaerobic fermentation that could lead to a rise in temperature in the substrate and to emission of methane which is detrimental since poisonous.

Furthermore, the ploughing is made such that trenches are created in the substrate, thus increasing the overall surface that is accessible to the insect, therefore improving the nutrient access. Also, the ploughing may allow the escaping of metabolic heats induced by the growth of the larvae and the fermentation of the substrate. Such metabolic heats may be used to improve the bioconversion process, as described hereafter.

Finally, ploughing can be made at the end of the bioconversion process, i.e. when the larvae are insects, to dry the substrate before the harvesting of the insect since the harvesting may be operated with the use of a sieve. Hence, the dry substrate may fall more easily than if it was wet, reducing the time needed to harvest the insects and improving the efficiency of the sieving process.

The action of ploughing can be decided according to different scenarios. In a first scenario, the action of ploughing is manually decided by an operator who considers that ploughing is needed at a particular moment. In a second scenario, the action of ploughing is automated and static. For example, the ploughing is made at each predetermined time interval (for example every day or every 12 hours). In a third scenario, the action of ploughing is automated and dynamic, meaning that ploughing is not performed at each predetermined time interval but when needed. For example, a system may determine that a ploughing is necessary based on data-driven system sensor data.

Another action performed by the mobile workstation 10 is to provide fluids to the substrate through spraying or any other fluid-delivering system. Another action is to perform measurements, in or close to the substrate, as will be described below.

Some or all of these actions may be performed simultaneously.

The aging phase typically lasts from 6 days to 18 days. When the operator 200 decides that the larvae (i.e. BSF) have reached maturity, he launches the substrate removal process.

In another embodiment, the substrate removal process may be automatically implemented according to a data-driven process, or may be automatically scheduled by an operator. When the substrate removal process is implemented for a container, the mobile workstation performs the process of removing the substrate from the corresponding container.

When the substrate removal process is implemented, the pusher 50 is activated by the controller. This function is ensured by the action of pressurized air at the level of the pusher 50. The pusher 50 then pushes from a few dozen centimeters to a few met of substrate out of the work area 3 to a reception area 56, for example into a collecting bin of the output module 54.

The movement is repeated until all the substrate is pushed out of the work area 3.

A cleaning phase can be added after the substrate removal process of a container 310. For example, the mobile workstation 10 is moved at one end of an empty container 310, and the brushes 60, 70 are activated, and the mobile workstation 10 is moved forward. Cleaning fluid, such as water or water-based liquid, may also be brought to the container 310 to be cleaned at that time, as described below. The mobile workstation 10 is moved forward with the brushes 60, 70 in operation, so as to clean the container. The output module 54 may comprise a specific waste receptacle, in order to receive the waste pushed through the exit by the brushes 60, 70, so that the waste is not mixed with the previously collected substrate.

Another function of the pusher 50 is to level the substrate. The pusher 50 is set in the upper position, and the orientation of the pusher 50 is set up in order that a portion of the pusher 50 is at the horizontal level of the desired level of substrate. This position of the pusher 50 is the equalizer position. When the pusher 50 is in the equalizer position, when the mobile workstation 10 is moving, the substrate level is equalized by the pusher 50. Further, the height of the equalizer position may vary during the rearing of the insects. Hence, the position and orientation of the pusher 50 in equalizer position may be different depending on the age of the substrate.

The mobile workstation 10 further comprises at least one sensor able to measure at least one relevant parameter regarding the status of the substrate or the status of the air.

The information of the sensors can be sent through a cable to the computer of the mobile workstation 10 and also through another cable to the remote computerized unit.

The sensors collect for example the temperature, the humidity, the level of oxygen in the air, the pH level of the substrate, etc. Two groups of sensors can be provided on the mobile workstation 10: the environmental sensors to measure parameters of the environment of the substrate, and the substrate sensors to measure parameters of the substrate.

Environmental sensors can be mounted on the structure of the mobile workstation 10 to measure parameters of the air nearby the substrate but outside the substrate.

Substrate sensors can be mounted on a stem part of the mobile workstation 10 and extended below the frame of the mobile workstation 10 to remain in the substrate when the mobile workstation 10 is moving. The shape of the sensor stem is designed to reduce the hindrance to the movement.

The sensor stem can also have an upper position and a lower position, according to the same principle as the tools described here above. Thus, the same sensor can be used alternatively as a substrate sensor or an environmental sensor.

The mobile workstation 10 is alimented by at least one vital resource for the development of living organisms, the vital resource being released by one dedicated system of the mobile workstation 10.

A humidification system is one vital resource for the development of living organisms that can be installed on the mobile workstation 10.

The water is provided through a water pipe from the source of water to the mobile workstation 10. The source of water can supply water at different temperatures between 1 and 40 degrees. Water may also be supplied mixed with organic nutriments. The pH of the supplied water can also be adjusted, which may in turn influence the pH of the substrate.

The injection of water may encourage the bioconversion process since the water will influence the temperature of the substrate. Ideally, the temperature of the water is chosen so the temperature of the substrate is optimal. The optimal temperature of the substrate to promote larvae growth may be comprised between 2° and 35° C. and may mostly depend on the insect to grow.

The water pipe is connected to one side of a valve that can be remotely controlled. On the other side of the valve, a network of drilled pipes is fixed on the mobile workstation 10.

A controller may control the release of one vital resource, such as air, water and/or nutrients, based on a monitoring of the above parameters measured by the sensors.

The farming installation 1 of the present application is moreover especially designed to favorize the bioconversion process while reducing the energy consumption needed to make the larvae grow, thus improving the overall efficiency of the farming installation.

A first way of achieving this it to maximize the thermic transfers in the farming installation 1 by filling the containers 310 according to a specific pattern linked to the age of the larvae present in the substrate.

More precisely, the insect larvae exhales heat differently regarding their growth stage. The smaller the larvae, the more heat they need to grow, while the older larvae tend to produce excess heat.

Hence, to reduce the energy consumption, each level is filled with substrate containing larvae at a specific growth stage, with the purpose of maximizing the age difference between two consecutive containers.

Advantageously, as much as possible, the containers of the farming installation are filed with an alternance of container containing older larvae and container containing younger larvae. This particular configuration allows to use the heat excess produced by the older larvae to help the youngest larvae to grow. This is a natural heat exchange that is exploited within the farming installation to promote growth and reduce energy consumption.

More precisely, the filling of the containers 310 may be spread over time, advantageously over days, where some containers 310 may be first filled with substrate containing seeded larvae, while some other containers may be left empty. The left-empty containers 310 may be filled after a few days with substrate containing seeded larvae. Advantageously, the left-empty containers may be consecutive to the already-filled containers. Hence, the already-filled containers, at the day where the left-empty containers are filled, contain substrate with older larvae. Hence, the seeded larvae contained in the newly-filled container may beneficiate from the heat exhaled by the older larvae contained in the already-filled containers.

The filling process of the containers 310 may be performed according to a specific and static schedule to maximize the age difference of the larvae/insect contained in two consecutive containers 310. Hereafter is a non-limitative example for larvae necessitating 7 days to grow. For example, at day 1, a first container 310 may be filled with substrate containing young larvae (i.e. seeded larvae), while the others are left empty. At day 2, another container 310 may be filled with substrate containing young larvae. The two containers 310 may not be consecutive. The process may continue with the filing on day 3 of a third container 310 with substrate containing young larvae. The third container 310 may not be consecutive with the first and second containers 310. At day 4, the container 310 between first and second may be filled with substrate containing young larvae, so the larvae in the container 310 4 will benefit from the metabolic heat delivered by the first and second containers 310, etc. At day 7, the first container 310 may be emptied to harvest the mature larvae and filled with a new substrate containing young larvae.

Of course, the filling process of the containers 310 also depends on the number of containers 310 in the installation.

In another embodiment, the filing process of the containers 310 may be performed according to a dynamic schedule. Such dynamic schedule may be based on data-driven system.

Figure 4:
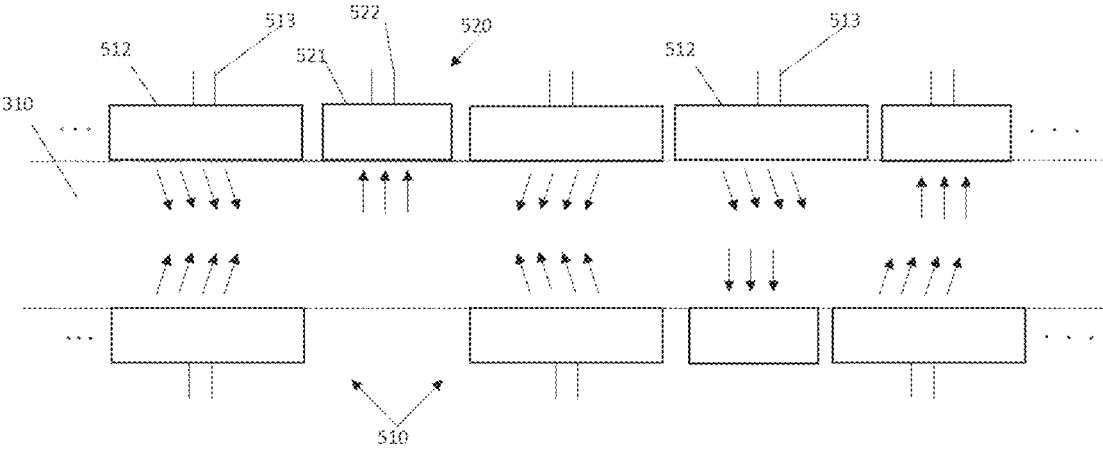
FIG. 4 represents a top view of a farming installation with a climate control system according to another embodiment.

The farming installation 1 may also comprise a climate control system 500 500, as illustrated on FIGS. 3 and 4.

The climate control system 500 is used to heat or cool the farming installation 1, and more precisely to adapt the temperature of the working area 3 as needed. When a container 310 is just loaded substrate containing seeded larvae, the larvae need some additional heat to help them start intensive growth. In this case the climate control system 500 provides warm air to help them keep warm and active. As the larvae increase their mass 10-10.000 times over the rearing period of 6 to 18 days their intensive metabolism produces significant quantities of body heat (metabolic heat). The climate control system 500 provides, in such scenario, air which is cooler than the larvae body mass. In general, the climate control system 500 aims to maintain the temperature of the air in the substrate in a range of 20-35 degrees centigrade.

The climate control system 500 generally comprises an air injection subsystem 510 and an air extraction subsystem 520.

The air injection subsystem 510 comprises an incoming air entry (not shown), connected with the outside, a plurality of incoming air outputs 512, each incoming air outputs 512 being linked to an incoming air duct 513 which comprises pipes and/or chimneys, and a fan configured to move the air from outside the farming installation 1 to the plurality of incoming air outputs 512.

In an embodiment, two incoming air outputs 512 are provided in the farming installation 1. The two incoming air outputs 512 may be placed symmetrically with regard to the longitudinal axis of the containers 310, such as to face each other. The two incoming air outputs 512 may be placed either at the entrance longitudinal end 4 of the installation 1 or at any place along a container 310. Such configuration allows to inject air according to a turbulent air flow.

The turbulent air flow presents several advantages compared to a laminar air flow.

First, when the ploughing is performed, the turbulent air flow helps to evacuate the metabolic gasses in a more efficient way, while injecting fresh air in the bottom of the substrate. Second, the turbulent airflow helps to reach the target temperature by promoting heat exchange between the substrate and the air. Third, the turbulent airflow allows to dry the substrate more efficiently at the harvesting step since the drying is more uniformly operated, therefore preventing the formation of a crust at the top surface of the substrate.

The ploughs 40 of the mobile workstation 10 may also be used in synergy with the climate control system 500 to promote the larvae growth. More precisely, when the sensors of the mobile workstation 10 register that a substrate moisture setpoint is achieved, the ploughs 40 of the mobile workstation 10 may be used iteratively, for example, to plough the substrate according to a certain depth, for example, from 5 cm below the substrate surface down to the whole thickness of 15 cm of the substrate, thereby mixing the dry substrate with the wet substrate to obtain a homogeneous mix on said depth. The time delay between two ploughing may be determined as described above.

In another embodiment, more than two incoming air outputs 512 are provided at each level of the farming installation 1. At each level (or in the single level when the air incoming outputs are disposed in the same level), the pair of incoming air outputs 512 are disposed at equidistance from one another according to the longitudinal direction of the farming installation 1 and above the substrate, to inject air in a homogeneous way along the working area, still according to a turbulent airflow.

The air extraction subsystem 520 comprises at least an air extraction entry 521, the air extraction entry 521 being linked to an extracted air duct 522, such as pipes and/or chimneys, an extracted air output and a fan configured to move the air from the air extraction entry 521 to the extracted air output.

In a particular embodiment, the air extraction entry 521 is positioned at the side of the opposed output end 13 of the farming installation 1, near the output module 54.

Hence, in the farming installation 1 the injected air can flow from entrance longitudinal end 4 or along the container 310 to the opposed output end 13 of each level of the farming installation 1, allowing the ventilation of the whole substrate at each level.

In another embodiment, two air extraction entries 521 are provided, facing each other to extract air homogenously.

This may be advantageous in the case where the containers only measure a few meters long. In the preferred embodiment where the containers measure at least a few dozen of meters, such configuration is not ideal since the air flow will become laminar at the level of the opposed output end.

Hence, in the embodiment where the containers measure at least a few dozens of meters, a plurality of extraction entries are provided. Each extraction entry may be spaced from a same predetermined distance from the others air extraction entries 521 to avoid leakage of air or metabolic gasses and to maximize their efficiency.

In a preferred embodiment, between each pair of incoming air outputs 512 may be provided an air extraction entry 521. Preferably, the air extraction entries 521 are placed on the same side of the installation (as illustrated on FIG. 3).

Alternatively, the air extraction entries 521 may be placed on both sides of the installation (or of a container). In an embodiment illustrated on FIG. 4, the air extraction entries 521 are alternatively placed on each side of the installation (or of a container), with regards to the longitudinal length of the installation. For example, a first extraction entry 521 is placed on a first side of the installation, a first pair of air extraction output is placed next to said first extraction entry 521, and a second extraction entry 521 is placed on the second side of the installation. The pattern may then be repeated along the length of the installation. This allows to provide turbulent air flow over the whole length of the containers 310.

Figure 5:
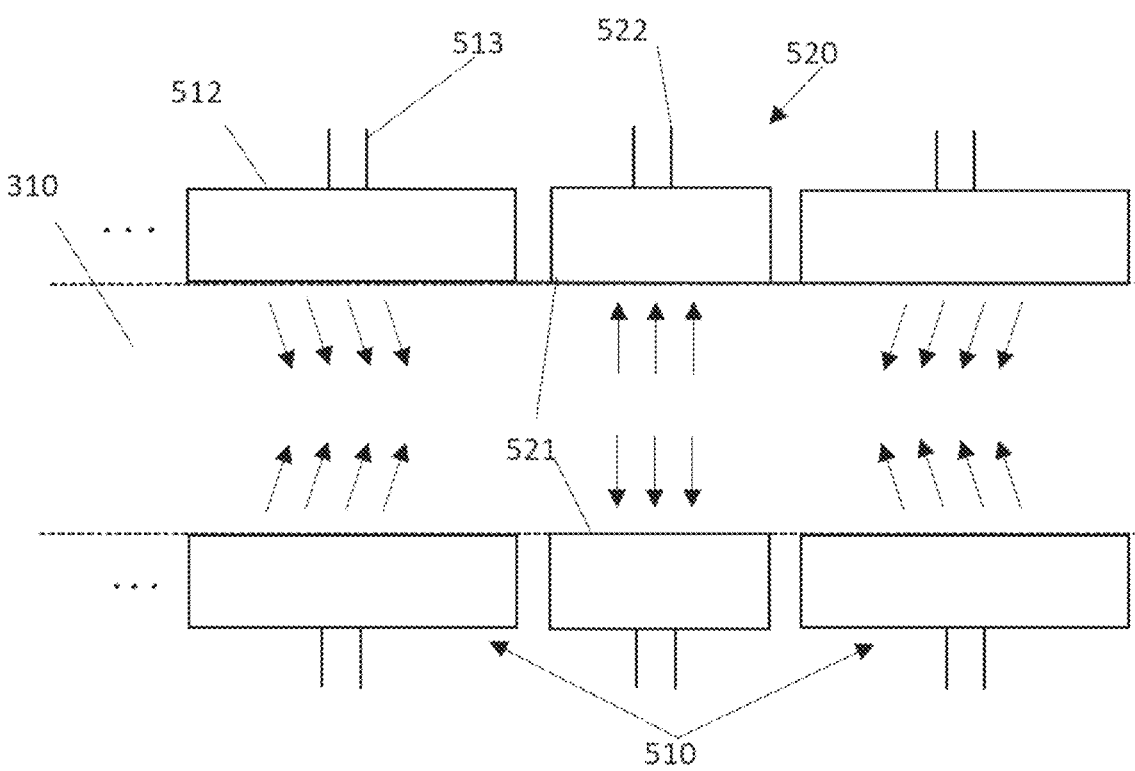
FIG. 5 represents a top view of a farming installation with a climate control system according to another embodiment.

In another embodiment illustrated on FIG. 5, a pair of extraction entries 521 facing each other may be placed.

The air extracted by the extraction subsystem 520 is the air that has been injected by the air incoming output of the climate control system 500 to the substrate. Sometimes, the extracted air is warmer than the injected air due to the heat exchange taking place between the larvae exhaling heat and the air flowing in the farming installation 1. Such warmer extracted air may furthermore be used to reduce the energy consumption. More precisely, the extracted air duct may be provided next to, or even in direct contact with, the incoming air duct such that the warmer extracted air may be used to heat the incoming air.

The climate control system 500 may further comprise a heat recovery system that picks up the warmer extracted air and injects it in the incoming air duct. More precisely, all the warmer extracted air or a portion of the warmer extracted air may be injected in the incoming air duct to fulfil a temperature criterion. The portion of the warmer extracted air injected in the incoming air duct may be chosen regarding the temperature of the incoming air. As a non-limitative example, if the air picked up outside in the incoming air duct is at a temperature of 5° C., up to 90% of the warmer extracted air may be injected in the incoming air duct. It may advantageously reduce the overall cost linked to the energy consumption of the installation.

The warmer extracted air may be first recycled before its injection in the incoming air duct. Optionally, a heat exchanger may further be used to reach the desire temperature.

To further enhanced the heat exchange between substrate located at different levels and the heat exchange within the farming installation 1 as such, the material of the containers 310 is chosen to allow and maximise heat transfer. Such material may present a high thermal conductivity (for example superior to 10 W m$^{-1}$ K$^{-1}$). Materials that can be used may comprise inox, aluminium, mild steel, glass fibre, plastic base with a thin metal coating, or a composite material. Inox may be the best material since it is easily washable, reusable, and anticorrosive.

The choice of the container 310 material allows to reduce the ventilation rate, thereby limiting the energy consumption of the farming installation 1.

While exemplary embodiment of the invention has been described with reference to the embodiments, it will be understood by those skilled in the art that various changes, omissions and/or additions may be made, and equivalents may be substituted for elements thereof without departing from the spirit and scope of the invention. In addition, many modifications may be made to adapt a particular situation or material to the teachings of the invention without departing from the scope thereof. Therefore, it is intended that the invention is not limited to the particular embodiment disclosed as the best mode contemplated for carrying out this invention, but that the invention will include all embodiments falling within the scope of the appended claims. Moreover, unless specifically stated any use of the terms first, second, etc. do not denote any order or importance, but rather the terms first, second, etc. are used to distinguish one element from another.

The invention claimed is:

1. A method for promoting a bioconversion of insects in an insect farming installation, said insect farming installation comprising a module comprising continuous profiled containers made of a thermally conductive material having a thermal conductivity of at least 10 W m$^{-1}$ K$^{-1}$, the continuous profiled containers being vertically superimposed to one another, said method comprising:

filling the containers with substrate containing seeded larvae such that an age difference of the larvae contained in the substrates respectively filling two consecutive containers is maximized.

2. The method according to claim 1, wherein the continuous profiled containers are filled such that one continuous profiled container filled with substrate containing younger larvae is located directly above one continuous profiled container filled with substrate containing older larvae.

3. The method according to claim 1, wherein the filling of two consecutive continuous profiled containers is performed by:

filling a first continuous profiled container with substrate containing seeded larvae;

leaving a second continuous profiled container empty, said second continuous profiled container being located above the and being consecutive to said first continuous profiled container; and after a chosen time, filing said second continuous profiled container with substrate containing seeded larvae, said chosen time corresponding to a time needed by the larvae to become mature larvae.

4. The method according to claim 1, wherein the farming installation further comprises a climate control system comprising an air injection subsystem, said air injection subsystem comprising a pair of incoming air outputs injecting air towards the continuous profiled containers, each incoming air outputs of said pair of incoming air outputs facing each other such that the injection subsystem injects air according to a turbulent flow.

5. The method according to claim 4, wherein the air injection subsystem comprises one pair of incoming air outputs per continuous profiled container, each pair of incoming air outputs being configured to inject air on the substrate contained in the corresponding continuous profiled container according to the turbulent flow.

6. The method according to claim 4, wherein the air injection subsystem comprises a plurality of pairs of incoming air outputs per continuous profiled container, each pair being disposed equidistantly from one another according to a longitudinal direction of said continuous profiled container.

7. The method according to claim 4, wherein the climate control system further comprises an air extraction subsystem comprising at least one air extraction entry adapted to extract the air injected by the air injection subsystem from the farming installation.

8. The method according to claim 7, wherein the air extraction subsystem comprises a plurality of air extraction entries per continuous profiled containers, said air extraction entries being adapted to extract the air injected by the air injection subsystem, an air extraction entry being placed between each pair of incoming air outputs per continuous profiled container.

9. The method according to claim 7, wherein the air injection subsystem is configured to inject air pumped from outside the farming installation, wherein the extracted air is warmer than the injected air and wherein the air extraction subsystem heats the air pumped by the air injection subsystem with the extracted air, before injecting said heated air pumped by the air injection subsystem.

10. The method according to claim 9, wherein the extracted air is recycled and injected in the air injection subsystem.

11. The method according to claim 1, wherein the farming installation further comprises a mobile workstation, said mobile workstation comprising a displacement system, said mobile workstation moving above the continuous profiled containers by mechanical cooperation with a guiding system of said automated insect farming installation, and said mobile workstation comprising an active system performing an action on the substrate, said action promoting a growth of the larvae contained in the substrate.

12. The method according to claim 11, wherein the active system comprises at least one plough ploughing the substrate.

13. The method according to claim 12, wherein the ploughing is performed according to a static schedule and/or according to a dynamic schedule, said dynamic schedule being dynamically adjusted according to a data-driven system.

14. The method according to claim 1, wherein a length of each container is equal or above 10 meters.

* * * * *